United States Patent
Kim et al.

(10) Patent No.: US 12,115,391 B2
(45) Date of Patent: Oct. 15, 2024

(54) RADIOGRAPHY AND RADIOTHERAPY APPARATUS

(71) Applicant: AURACARE CO., LTD., Yongin-si (KR)

(72) Inventors: Dong Wook Kim, Namyangju-si (KR); Dong Oh Shin, Seoul (KR); Yeong Geol Bae, Yongin-si (KR); Hyeon Tae Kyeong, Seoul (KR)

(73) Assignee: AURACARE CO., LTD., Yongin-si Gyeonggi-do (KR)

( * ) Notice: Subject to any disclaimer, the term of this patent is extended or adjusted under 35 U.S.C. 154(b) by 601 days.

(21) Appl. No.: 17/333,920

(22) Filed: May 28, 2021

(65) Prior Publication Data

US 2021/0283425 A1 Sep. 16, 2021

Related U.S. Application Data

(63) Continuation of application No. PCT/KR2019/016786, filed on Nov. 29, 2019.

(30) Foreign Application Priority Data

Nov. 30, 2018 (KR) .................. 10-2018-0152000

(51) Int. Cl.
*A61N 5/10* (2006.01)
*A61B 6/00* (2006.01)
(Continued)

(52) U.S. Cl.
CPC .......... *A61N 5/1067* (2013.01); *A61B 6/032* (2013.01); *A61B 6/035* (2013.01); *A61B 6/06* (2013.01);
(Continued)

(58) Field of Classification Search
CPC ....... A61B 6/032; A61B 6/035; A61B 6/0407; A61B 6/0492; A61B 6/06; A61B 6/08;
(Continued)

(56) References Cited

U.S. PATENT DOCUMENTS

| | | | |
|---|---|---|---|
| 2011/0142202 A1 | 6/2011 | Brown et al. | |
| 2013/0231516 A1* | 9/2013 | Loo ..................... | A61N 5/1065 600/1 |
| 2018/0303452 A1 | 10/2018 | Bernhardt et al. | |

FOREIGN PATENT DOCUMENTS

| | | |
|---|---|---|
| EP | 2634775 A1 | 9/2013 |
| JP | H10179565 A | 7/1998 |

(Continued)

OTHER PUBLICATIONS

International Search Report of PCT/KR2019/016786 dated Mar. 11, 2020.

*Primary Examiner* — Mark R Gaworecki
(74) *Attorney, Agent, or Firm* — Dinsmore & Shohl LLP; Yongsok Choi, Esq.

(57) ABSTRACT

A radiography and radiotherapy apparatus comprises a body unit, a gantry configured to rotate relative to the body unit, a treatment table on which an object is placed and configured to slide into holes formed in the body unit and the gantry and move in a vertical direction, a gantry driving part configured to rotate the gantry, a radiation irradiation part mounted on the gantry and configured to irradiate radiation toward the object, an image detector mounted to face the radiation irradiation part in the gantry and configured to detect the radiation irradiated from the radiation irradiation part, and a beam stopper provided at a lower end of the image detector and configured to block the radiation.

4 Claims, 4 Drawing Sheets

(51) Int. Cl.
*A61B 6/03* (2006.01)
*A61B 6/06* (2006.01)
*A61B 6/10* (2006.01)
*A61B 6/40* (2024.01)
*A61B 6/04* (2006.01)

(52) U.S. Cl.
CPC ............ *A61B 6/107* (2013.01); *A61B 6/4035* (2013.01); *A61B 6/4435* (2013.01); *A61B 6/54* (2013.01); *A61B 6/542* (2013.01); *A61N 5/1045* (2013.01); *A61N 5/1069* (2013.01); *A61N 5/1071* (2013.01); *A61N 5/1081* (2013.01); *A61B 6/0407* (2013.01); *A61B 6/0492* (2013.01); *A61B 6/4429* (2013.01); *A61N 5/103* (2013.01); *A61N 2005/1054* (2013.01); *A61N 2005/1063* (2013.01); *A61N 2005/1094* (2013.01); *A61N 2005/1095* (2013.01)

(58) Field of Classification Search
CPC ..... A61B 6/107; A61B 6/4035; A61B 6/4275; A61B 6/4405; A61B 6/4429; A61B 6/4435; A61B 6/54; A61B 6/542; A61B 6/583; A61N 5/103; A61N 5/1045; A61N 5/1067; A61N 5/1069; A61N 5/1071; A61N 5/1081; A61N 2005/105; A61N 2005/1054; A61N 2005/1063; A61N 2005/1094; A61N 2005/1095
See application file for complete search history.

(56) References Cited

FOREIGN PATENT DOCUMENTS

| | | | | |
|---|---|---|---|---|
| JP | 2017213184 | A | 12/2017 | |
| KR | 1020130131390 | A | 12/2013 | |
| KR | 101649413 | B1 | 8/2016 | |
| KR | 1020180010758 | A * | 1/2018 | |
| KR | 1020180050959 | A | 5/2018 | |
| WO | WO-2009138753 | A1 * | 11/2009 | ........... A61N 5/1049 |
| WO | WO-2017100611 | A1 * | 6/2017 | ............. A61B 6/032 |

\* cited by examiner

RADIOGRAPHY AND RADIOTHERAPY APPARATUS

CROSS-REFERENCE TO RELATED APPLICATIONS

This application is a continuation of PCT/KR2019/016786 filed on Nov. 29, 2019 which claims priority to Korean Patent Application No. 10-2018-0152000 filed on Nov. 30, 2018, the entire contents of which are herein incorporated by reference.

TECHNICAL FIELD

The present disclosure relates to a radiography and radiotherapy apparatus.

BACKGROUND

A simulated treatment and a treatment planning are required prior to radiotherapy. In the simulated treatment, a computerized tomography (CT) simulator that performs a CT imaging or an X-ray simulator that performs an X-ray imaging is used. The treatment planning is performed based on images obtained by the CT imaging or the X-ray imaging.

In the simulated treatment based on the CT imaging, an image of the interior of an object is captured in the form of a cross-section by using a rotating X-ray tube and a detector. The image of the CT imaging performed for the simulated treatment provides image information on soft-tissues, such as blood, cerebrospinal fluid, gray matter, white matter, tumor, and the like, which are difficult to identify in the general X-ray imaging. By reconstructing such image information, three-dimensional image information can be obtained.

A CT imaging machine and an X-ray imaging machine for the simulated treatment are installed separately. In addition, after the simulated treatment and the treatment planning are performed, an equipment for radiotherapy is also installed separately. That is, a radiography machine for a simulated treatment and a radiotherapy machine for an actual treatment are installed separately. This may cause two disadvantages. First, such a separate installation is disadvantage in terms of cost and space. Since both the radiography machine and the radiotherapy machine emit radiation harmful to a human body, a shielding facility needs to be necessarily installed in the places where they are installed. In the case in which the radiography machine and the radiotherapy machine are provided separately, two shielding facilities need to be installed, respectively. This results in an increase in cost for installing the apparatus. In addition, a large space in which the apparatus is installed is required. This makes it difficult for a small-scale hospital or animal hospital to install both the radiography machine and the radiotherapy machine.

Second, the separate installation makes it difficult to perform the radiotherapy immediately after performing diagnosis based on the radiography. If the radiography machine and the radiotherapy machine are installed separately, a one-stop treatment, which performs both the radiography and the radiotherapy using a single apparatus becomes technically impossible.

Korean patent laid-open publication No. 2013-0131390 and Japanese laid-open publication No. H10-179565 are incorporated herein by references as patent documents of prior art documents in the related art.

SUMMARY

The present disclosure is made in view of the above problems, and an object of the present disclosure is to provide an apparatus capable of performing both radiography and radiotherapy.

Furthermore, an object of the present disclosure is to provide an apparatus using a single radiation source in performing both radiography and radiotherapy.

A radiography and radiotherapy apparatus according to one embodiment of the present disclosure includes a body unit, a gantry configured to rotate relative to the body unit, a treatment table on which an object is placed and configured to slide into holes formed in the body unit and the gantry and move in a vertical direction, a gantry driving part configured to rotate the gantry, a radiation irradiation part mounted on the gantry and configured to irradiate radiation toward the object, an image detector mounted to face the radiation irradiation part on the gantry and configured to detect the radiation irradiated from the radiation irradiation part, and a beam stopper provided at a lower end of the image detector and configured to block the radiation. The radiation irradiation part includes a radiation source configured to generate the radiation, a primary collimator configured to shield the radiation generated from the radiation source and determine a beam dispersion angle, a variable filter part configured to adjust an intensity of the radiation from the primary_collimator, an ion chamber configured to monitor a dose of the radiation from the variable filter part, and a multi-leaf collimator configured to adjust a distribution of the dose of the radiation from the ion chamber.

In some embodiments, a shielding box may be provided to surround the body unit as a whole. The shielding box may be made of a shieldable material such as opaque lead or other metallic materials, non-metallic material such as concretes, or a lead glass. Thus, the radiography and radiotherapy apparatus according to an embodiment of the present disclosure may have a self-shielding function.

The radiography and radiotherapy apparatus according to the present disclosure may further include additional features.

According to the present disclosure, it is possible to provide an apparatus capable of performing both radiography and radiotherapy.

Furthermore, according to the present disclosure, it is possible to provide an apparatus using a single radiation source in performing both radiography and radiotherapy.

DETAILED DESCRIPTION OF THE PREFERRED EMBODIMENTS

Hereinafter, preferred embodiments of the present disclosure will be described in detail with reference to the appended drawings to such an extent that the present disclosure can be readily practiced by one of ordinary skill in the art.

Detailed descriptions of parts irrelevant to the present disclosure will be omitted for the purpose of more clearly describing the present disclosure, and the sizes, thicknesses, positions, and the like of the respective components shown in the drawings are arbitrarily shown for the sake of convenience in description, and hence the present disclosure is not necessarily limited thereto. That is, it should be understood that specific shapes, configurations, and characteristics described in the specification may be modified in various embodiments without departing from the spirit and scope of the prevent disclosure, and positions or arrangements of individual components may be modified without departing from the spirit and scope of the prevent disclosure.

Therefore, detailed descriptions to be described below should be construed as non-limitative senses, and the scope of the prevent disclosure should be understood to include appended claims and their equivalents.

Overall Configuration of Apparatus

An overall configuration of a radiography and radiotherapy apparatus 100 according to an embodiment of the present disclosure will be described with reference to FIGS. 1 and 2.

The radiography and radiotherapy apparatus 100 according to an embodiment of the present disclosure is, for example, an apparatus for treating animals, such as a mouse, a cat and a dog by radiography and radiotherapy. However, the scope of the present disclosure is not limited to the radiography and radiotherapy for animals. The apparatus of the present disclosure may be used for the purpose of radiography and radiotherapy for human being.

The radiography and radiotherapy apparatus 100 according to an embodiment of the present disclosure includes a body unit 10. The body unit 10 is a unit functioning as a body of the radiography and radiotherapy apparatus 100, namely a framework, as the name of the respective component implies. The body unit 10 performs a function of the framework of the entire apparatus and a function of a frame on which various driving parts are mounted. As shown in FIGS. 1 and 2, a hole is formed in the body unit 10. The hole forms a space to which an object to be subjected to radiography and radiotherapy is moved. As shown in FIGS. 1 and 2, a support plate may be provided in a lower end of the body unit 10. A plurality of wheels may be provided in a lower end of the support plate. The radiography and radiotherapy apparatus 100 according to an embodiment of the present disclosure may have a movable structure using the plurality of wheels. Although not shown in FIGS. 1 and 2, a shielding box may be provided so as to surround the body unit 10 as a whole. The shielding box may be made of a shieldable material, such as a lead glass. Thus, the radiography and radiotherapy apparatus 100 according to an embodiment of the present disclosure may have a self-shielding function.

A gantry 20 is provided inward of the body unit 10. The gantry 20 has a hole corresponding to the shape and size of the hole of the body unit 10. The gantry 20 is coupled to the body unit 10 in a rotatable manner. The gantry 20 is connected to a gantry driving part 40. In the embodiment shown in FIGS. 1 and 2, the gantry driving part 40 includes an electric motor that generates a rotational driving force, a pulley connected to the electric motor, and a belt for connecting the pulley and the gantry 20. The gantry 20 rotates relative to the body unit 10 with the operation of the gantry driving part 40. In the embodiment shown in FIGS. 1 and 2, the gantry driving part 40 transmits the rotational driving force to the gantry 20 using the electric motor and the belt, but the configuration of the gantry driving part 40 is not limited to the embodiment. As an example, any driving manner that can rotate the gantry 20 relative to the body unit 10 may be included in the scope of the present disclosure. The gantry 20 performs a frame function as a base on which a radiation irradiation part 50 configured to irradiate the object with radiation in the state in which the object is located inside the gantry 20 (i.e., in the aforementioned hole) so as to be subject to the radiography and radiotherapy, an image detector 60 configured to detect the radiation irradiated from the radiation irradiation part 50 and passing through the object, and a beam stopper 70 configured to block further travelling of the radiation are mounted. When the gantry 20 rotates with the operation of the gantry driving part 40, the radiation irradiation part 50, the image detector 60, and the beam stopper 70 mounted on the gantry 20 also rotate. The rotation of the gantry 20, and the radiation irradiation part 50, the image detector 60, and the beam stopper 70 mounted on the gantry 20 is performed such that the object is irradiated with the radiation at an optimal position.

The treatment table 30 can move through the holes of the body unit 10 and the gantry described above. The object is placed on the treatment table 30 so as to be subjected to the radiography or radiotherapy. In FIG. 1, the treatment table 30 is shown to be located outside the body unit 10 and the gantry 20, but it may be moved into the holes of the body unit 10 and the gantry 20 in a sliding manner during the radiography or radiotherapy. A lower support portion of the treatment table 30 may include a cylinder that is displaceable upward or downward in a vertical direction. By such an operation of the cylinder, the treatment table 30 is movable upward or downward. The vertical movement of the treatment table 30 is performed to optimize the position of the object during the radiography or radiotherapy. Through the rotation of the gantry 20 and the sliding movement and vertical movement of the treatment table 30, the object may be subjected to the radiography or radiotherapy at the optimal position. A driving control of all movable components of the radiography and radiotherapy apparatus 100 is controlled by a control device (to be described later).

Figure 4:
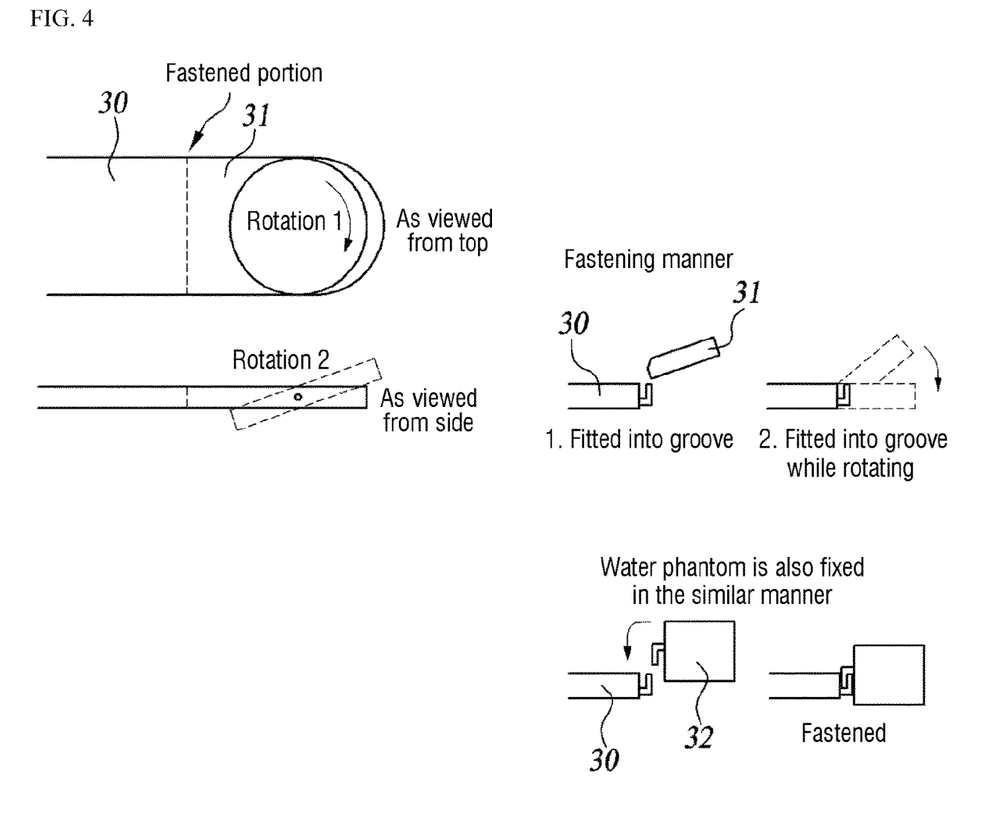
FIG. 4 shows a rotary table or a water phantom that can be mounted on a treatment table of the radiography and radiotherapy apparatus according to an embodiment of the present disclosure.

A rotary table 31 may be provided at an end of the treatment table 30. The rotary table 31 is particularly advantageous when the object is a small animal. When the small animal, such as a cat, a mouse, and a small dog, is placed as an object on the rotary table 31, the object may be further rotated at a specific angle even after the setting is performed. The rotation of the object by the rotary table 31 is advantageous in setting an optimal posture during the radiography or radiotherapy. The rotation manner of the rotary table 31 and the connection manner of the rotary table 31 and the treatment table 30 are shown in FIG. 4. As shown in FIG. 4, the rotary table 31 is rotatable clockwise or counterclockwise as viewed from above. Such a clockwise or counterclockwise rotation is indicated by a rotation 1 in FIG. 4. In addition, the rotary table 31 may be coupled to both sides of the treatment table in a hinge manner so that the rotary table 31 is swingable relative to the treatment table as viewed from side. Such a swing operation is indicated by a rotation 2 in FIG. 4.

The aforementioned rotary table 31 is detachably fastened to the treatment table 30. One example of such a fastening manner is shown in the right side of FIG. 4. A groove corresponding to a fixture mounted to the treatment table 30 may be formed in the rotary table 31. The rotary table 31 may be fastened to the treatment table 30 by inserting the fixture of the treatment table 30 into the groove of the rotary table 31. The rotary table 31 may be detached from the treatment table 30 by releasing the fixture from the groove. The aforementioned fastening manner is applicable even when a water phantom is mounted to the treatment table 30. Instead of the rotary table 31, a water phantom 32 for dose measurement tailored to the small animal may be mounted to the treatment table 30. In this case, the water phantom 32 may be connected to the treatment table 30 by fitting the fixture of the treatment table 30 into a groove of the water phantom 32. Alternatively, as shown in FIG. 4, the water phantom 32 may be connected to the treatment table 30 by coupling a fixture of the water phantom 32 to the fixture of the treatment table 30.

A posture of the object placed on the treatment table 30 may be preferably secured by a fixing member (not shown). When the object placed on the treatment table 30 is an animal not the human being, the posture of the object is required to be further fixed. The fixing member may be formed of a material that is flexibly deformable in conformity to the object and does not interfere with the radiation. The fixing member minimizes the motion of the object and fixes the position of the object and the posture of the object during the radiography and radiotherapy. More specifically, when the object is an animal, various types of fixing members may need to be used considering physical characteristics different from those of the human being. As an example, since the animal is fixed to the rotary table 31 while wearing a mask for anesthesia, an appropriate fixing member adapted for the state of the animal may be selected and used. The radiography and radiotherapy apparatus 100 according to the present disclosure may include a compensator (not shown) as a component configured to make a dose distribution suitable for the radiography and radiotherapy of the fixed object. The compensator may be attached to the aforementioned fixture or a head of a treatment device. The compensator may be a thick material and may be positioned on the object to attenuate the intensity of the radiation when the object is irradiated with the radiation. According to a type of the compensator, the dose distribution of the radiation irradiated toward the object may be controlled as desired.

When the object is an animal, the animal needs to be anesthetized as described above. In the case in which the radiography and radiotherapy apparatus 100 according to the present disclosure has the self-shielding function, the radiography and radiotherapy apparatus 100 requires a space to which a tube extending from an external anesthesia equipment is inserted. Accordingly, the self-shielding wall of the radiography and radiotherapy apparatus 100 preferably includes a device through which the tube extending from the external anesthesia equipment passes or to which the tube is connected in a state in which the shielding effect is kept. Alternatively, the anesthesia equipment may be provided within the self-shielding wall. This eliminates a need for the device through which the tube extending from the external anesthesia equipment passes or to which the tube is connected.

A laser device (not shown) used for setting the object may be included in the radiography and radiotherapy apparatus 100 according to an embodiment of the present disclosure. The laser device may be located in the body of the radiography and radiotherapy apparatus 100, and may be further provided in the shielding wall described above. Three laser devices may be provided on the top face, left and right faces of the radiography and radiotherapy apparatus 100, respectively. Each laser provided by the laser devices has a cross line shape (the laser projected onto the shielding wall has a line laser shape rather than a spot and has the form of a cross line rather than a single line). The laser is used to accurately set the position and posture of the object when the object is placed on the treatment table by matching a small cross line indicated on the object or the fixture in three directions.

A real-time radiation dose measurement device may be provided in the aforementioned self-shielding wall or at a proper position of the body of the apparatus protected by the shielding wall. In some embodiments, in addition to the real-time radiation dose measurement device, a device configured to measure temperature and humidity and compile a database of the measured results may be additionally provided. By utilizing these devices, it is possible to obtain data for an accumulated dose over a month or year. In some embodiments, in addition to the real-time dose measurement device described above, a device configured to issue an automatic alarm and stop the irradiation of the radiation when the dose exceeds a predetermined maximum value, may be further provided.

Configuration of the Radiation Irradiation Part

As described above, the radiation irradiation part 50 is mounted to the gantry 20. The radiation irradiation part 50 rotates around the object with the rotation of the gantry 20 while being mounted to the gantry 20. The radiation irradiated from the radiation irradiation part 50 penetrates through the object and reaches the image detector 60. In the case in which the radiography and radiotherapy apparatus 100 according to an embodiment of the present disclosure is used for radiography, the image detector 60 detects the radiation penetrating through the object and transmits the detection result to the control device. A software installed on the control device converts signals detected by the image detector 60 into an image. The beam stopper 70 is provided in the lower end of the image detector 60 to block the radiation from further travelling.

A detailed configuration of the radiation irradiation part 50 will be described with reference to FIG. 3. In an embodiment shown in FIG. 3, the radiation irradiation part 50 includes a radiation source 51, a primary collimator 52, a filter part 53, an ion chamber 54, and a multi-leaf collimator 55. The function of each component will now be briefly described. First, the radiation source 51 generates radiation required for radiography or radiotherapy. The primary collimator 52 shields the radiation generated from the radiation source 51 and determines a beam dispersion angle. The filter part 53 performs a function of adjusting the intensity of the radiation by passing only a portion of the radiation that has passed through the primary collimator 52. The filter part 53 may include a plurality of filters provided therein to adjust the intensity of the radiation as described above. The arrangement of the plurality of filters may be varied. In view of this feature, the filter part 53 may be referred to as a variable filter part. The ion chamber 54 monitors the radiation dose. The multi-leaf collimator 55 is located at an end of the radiation irradiation part 50 to adjust a distribution of the radiation dose.

In the present disclosure, a compensator may be provided at an end of the head or on a surface of the object to be subjected to the treatment and to be irradiated with the radiation. The compensator adjusts the intensity of the radiation irradiated toward the object from the radiation source and guides the radiation having the adjusted intensity to the object. The compensator may include the aforementioned multi-leaf collimator 55. In a modification, for example, a three-dimensional printer or a three-dimensional compensator manufactured by a molding unit may be provided to adjust an amount of transmitted energy beam. The three-dimensional compensator has such a shape that a dose is increased in a region of the object where radiography and radiotherapy is required, and only a minimum amount of dose is transmitted to an unnecessary peripheral region. The shape and size of the compensator is not limited to the above description.

A primary feature of the radiography and radiotherapy apparatus 100 according to the present disclosure includes performing both radiography and radiotherapy. A secondary feature of the radiography and radiotherapy apparatus 100 according to the present disclosure includes performing both radiography and radiotherapy using a single radiation source. These features are implemented by the radiation irradiation part 50 of the present disclosure. There is a difference in energy levels of radiation for radiography and radiotherapy. The energy level for radiography may be in a range of approximately 10 to 100 kV. The energy level for radiotherapy may be in a range of approximately 100 to 500 kV. A radiography machine and a radiotherapy machine, which are being generally used, employ sources for generating radiation of energy levels suitable for respective purposes. However, the radiography and radiotherapy apparatus 100 according to the present disclosure employs the radiation source 51 capable of generating the radiation of energy level enough for radiotherapy in order to perform both radiography and radiotherapy. The intensity of the radiation generated from the radiation source 51 is adjusted while reaching the filter part 53. In the embodiment shown in FIG. 3, the filter part 53 is rotatable. The filter part 53 may include the plurality of filters. Any one of the plurality of filters may be selected by the rotation of the filter part 53. Each of the plurality of filters of the filter part 53 may reduce the intensity of the radiation introduced into the filter part 53 to a predetermined intensity. Target intensities to be reduced by respective filters are different from each another. For example, when the radiography and radiotherapy apparatus 100 according to the present disclosure is used for radiography, a filter capable of converting the energy of the radiation generated from the radiation source 51 into low energy suitable for radiography, may be selected and used. When the radiography and radiotherapy apparatus 100 according to the present disclosure is used for radiotherapy, a filter capable of converting the energy of the radiation generated from the radiation source 51 into energy higher than the aforementioned energy suitable for radiography, may be selected and used. In addition to the filter part 53 as described above, the multi-leaf collimator 55 may be provided as a component for adjusting the radiation intensity. The multi-leaf collimator 55 adjusts the intensity of radiation irradiated onto a specific location in a predetermined range by adjusting the distribution of the radiation dose. However, since the radiography and radiotherapy apparatus 100 of the present disclosure is an apparatus capable of performing both radiography and radiotherapy, it is almost impossible to eliminate a difference in intensity of the radiation used for radiography and radiotherapy through the adjustment of the distribution of the radiation dose by the multi-leaf collimator 55. For this reason, the filter part 53 described above is an essential component in performing both radiography and radiotherapy with a single apparatus.

The ion chamber 54 monitors an amount of dose of the radiation passing through the filter part 53 in real time. The ion chamber 54 may be feedback-controlled. The monitoring results of the ion chamber 54 are transmitted to the control device. As described above, the radiography and radiotherapy apparatus 100 according to the present disclosure is used for both radiography and radiotherapy and converts the energy level of the radiation generated from the single radiation source using the filter part 53 according to the purpose of radiography or radiotherapy. Thus, it is important to monitor whether the energy level conversion result is in a desired degree. While the radiography and radiotherapy apparatus 100 is being operated for radiography, when the object is irradiated with the radiation of an energy level adapted for radiotherapy due to an erroneous control of the filter part 53, there may be a risk of damaging the object. Therefore, continuously monitoring the dose of the radiation passing through the filter part 53 is very important in the operation of the radiography and radiotherapy apparatus 100 according to the present disclosure. The control device receives the monitoring result of the ion chamber 54 and determines whether a value of the radiation dose meets a level of an intended purpose in real time. When it is determined that the value of the radiation dose is smaller than the level of the intended purpose, the control device may control the filter part 53 such that the radiation of a higher energy level is irradiated. When it is determined that the value of the radiation dose is excessively larger than the level of the intended purpose, the control device may control the filter part 53 such that the energy level of the radiation is reduced, or may control the radiation source 51 to stop the emission of the radiation. The radiation dose may be detected based on information detected by the image detector 60 described above, instead of using the ion chamber 54. Since there is a great need to prevent radiation of unintended intensity from reaching the object, the ion chamber 54 is disposed at the downstream of the filter part 53 and at the upstream of the multi-leaf collimator 55, which is a component through which the radiation finally passes just before reaching the object, to monitor the radiation dose at the respective position in real time.

Figure 1:
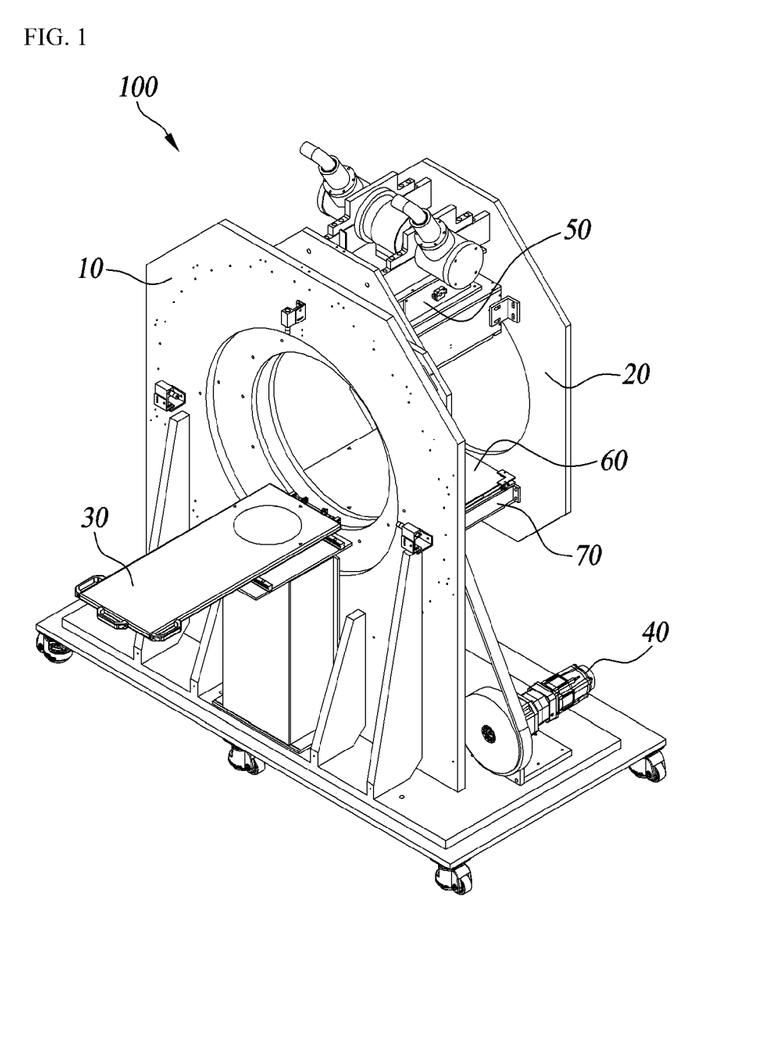
FIG. 1 is a perspective view of a radiography and radiotherapy apparatus according to an embodiment of the present disclosure.
Figure 2:
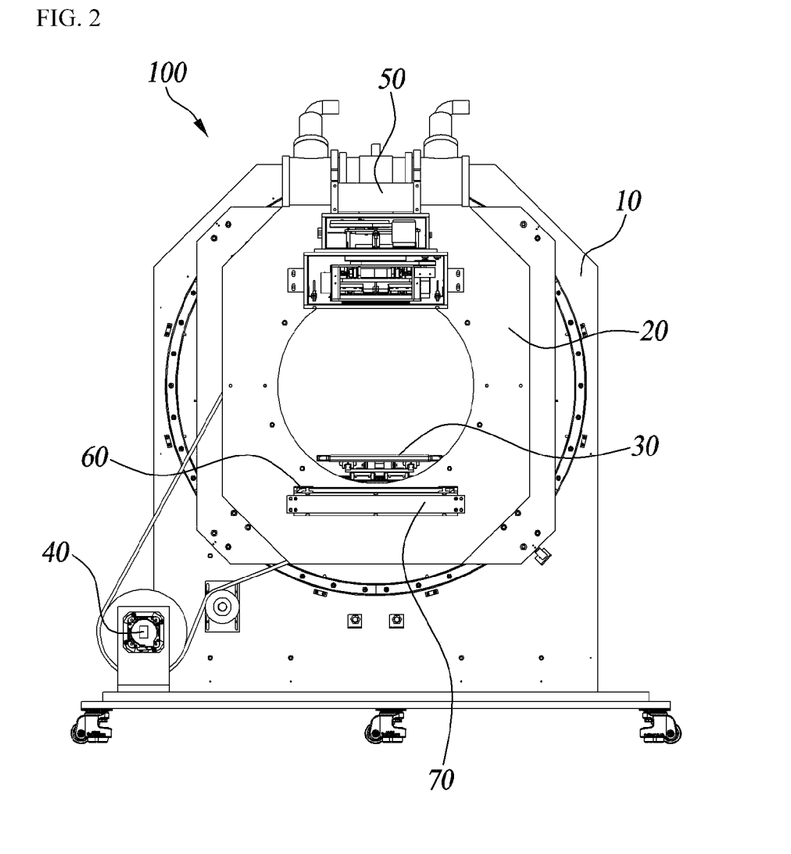
FIG. 2 is a front view of a radiography and radiotherapy apparatus according to an embodiment of the present disclosure.

In the embodiment shown in FIGS. 1 and 2, the radiation irradiation part 50 of the present disclosure has been described to be mounted to the gantry 20 and rotate together with the gantry 20 with the rotation of the gantry 20 by the gantry driving part 40. However, at least a portion of the radiation irradiation part 50 of the present disclosure may not be rotated. For example, the radiation source 51 of the radiation irradiation part 50 of the present disclosure may be positioned in a certain place of the body unit 10 so as not to rotate. The radiation generated from the radiation source 51 may be transmitted to the primary collimator 52, the filter part 53, the ion chamber 54, the multi-leaf collimator 55 and the like by a radiation inducing manner well known in the technical field of the present application. It should be understood that embodiments in which other components constituting the radiation irradiation part 50 are not disposed in the rotating gantry 20 are also included within the scope of the present disclosure.

Configuration of the Control Device

Figure 3:
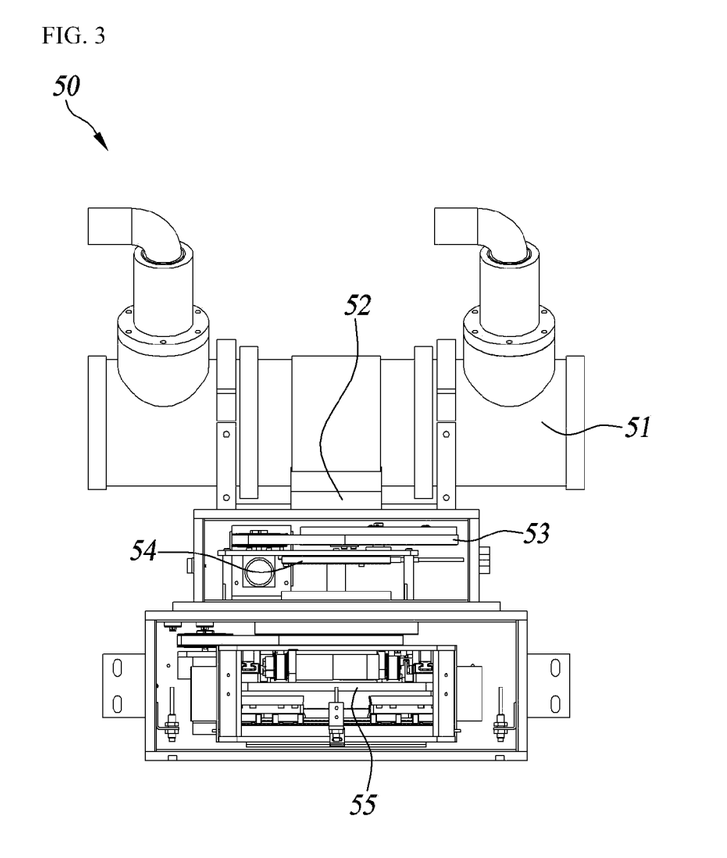
FIG. 3 shows a radiation irradiation part of the radiography and radiotherapy apparatus according to an embodiment of the present disclosure.

All components of the radiography and radiotherapy apparatus 100 described thus far are controlled by the control device not shown in FIGS. 1 to 3. The function of the control device in view of control of the apparatus is summarized as follows. First, the control device controls the movements of all movable components. The control device controls the vertical movement and the sliding movement of the treatment table 30, and the rotation of the gantry 20 so that the radiography or radiotherapy is performed at an optimal position. In addition, the control device may receive information on the real-time monitored radiation dose from the ion chamber 54 and control the filter part 53 or the like such that a desired energy level of radiation is transmitted to the object. When it is determined that the respective energy level is dangerous for the object, the control device urgently stops the overall operation of the apparatus or the radiation generation operation. In addition, the control device incorporates a software for producing an image that can be easily read by a medical personnel who plans the treatment, based on the detection data received from the image detector 60.

Further, one of major features of the control device of the present disclosure includes a treatment planning system. It is preferable that the radiography and radiotherapy apparatus 100 according to the present disclosure is configured to make a treatment plan in parallel with the radiography, and to perform the radiotherapy without delay based on the treatment plan. Since the treatment planning system is included in the control device, it is possible to calculate the optimal direction, pattern, and dose of radiation to be irradiated toward the object using video materials acquired during the radiography. The medical personnel checks the information calculated by the treatment planning system in-situ and utilizes the same for the radiotherapy. Treatment and video data transmitted to the control device may be shared or distributed in the form of big data over the Internet by a suitable encryption means and/or anonymization means. Accumulated data related to the radiotherapy may be used as a valuable reference for safer and more effective treatment in the future, and may have a large economic value as its own.

While the present disclosure has been described above by way of particular features such as specific components and the like, and exemplary embodiments and the drawings, these embodiments are provided to further facilitate overall understanding of the present disclosure, and the present disclosure is not limited thereto. Various modifications and variations may be made from the above descriptions by those skilled in the art.

Therefore, the spirit of the present disclosure should not be limited to the above-described embodiments, and not only the append claims but also all those modified equally or equivalently to the claims are intended to fall within the scope of the spirit of the present disclosure.

What is claimed is:

1. A radiography and radiotherapy apparatus, comprising:
a body unit;
a gantry configured to rotate relative to the body unit;
a treatment table on which an object is placed and configured to slide into holes formed in the body unit and the gantry and move in a vertical direction;
a gantry driving part configured to rotate the gantry;
a radiation irradiation part mounted on the gantry and configured to irradiate radiation toward the object;
an image detector mounted to face the radiation irradiation part on the gantry and configured to detect the radiation irradiated from the radiation irradiation part; and
a beam stopper provided at a lower end of the image detector and configured to block the radiation,
wherein the radiation irradiation part comprises:
a radiation source configured to generate the radiation;
a primary collimator configured to shield the radiation generated from the radiation source and determine a beam dispersion angle;
a variable filter part configured to adjust an intensity of the radiation from the primary collimator;
an ion chamber configured to monitor a dose of the radiation from the variable filter part; and
a multi-leaf collimator configured to adjust a distribution of the dose of the radiation from the ion chamber;
wherein the radiation irradiation part comprises a single radiation source, and the variable filter part adjusts an intensity of the radiation irradiated from the single radiation source to obtain a radiation dose suitable for both radiography and radiotherapy, and
wherein the treatment table comprises a rotary table provided at an end of the treatment table and detachable fastened thereto.

2. The radiography and radiotherapy apparatus of claim 1, wherein the variable filter part comprises a plurality of rotatable filters, and different filters are selected for the radiography and the radiotherapy, respectively.

3. The radiography and radiotherapy apparatus of claim 2, further comprising: a control device,
wherein the control device comprises a treatment planning system configured to calculate a direction, pattern, and dose of the radiation to be irradiated toward the object using image materials acquired during the radiography.

4. The radiography and radiotherapy apparatus of claim 3, wherein the body unit is located inside a shielding box formed of a shieldable material including a lead glass.

* * * * *